United States Patent
Dillon et al.

(10) Patent No.: US 8,477,318 B2
(45) Date of Patent: Jul. 2, 2013

(54) OPTICAL FIBER-BASED THREE-DIMENSIONAL IMAGING SYSTEM

(75) Inventors: Robert F. Dillon, Bedford, NH (US); Yi Qian, Acton, MA (US); Gurpreet Singh, Providence, RI (US)

(73) Assignee: Dimensional Photonics International, Inc., Wilmington, MA (US)

( * ) Notice: Subject to any disclaimer, the term of this patent is extended or adjusted under 35 U.S.C. 154(b) by 470 days.

(21) Appl. No.: 12/738,207

(22) PCT Filed: Oct. 23, 2008

(86) PCT No.: PCT/US2008/080943
§ 371 (c)(1),
(2), (4) Date: Apr. 15, 2010

(87) PCT Pub. No.: WO2009/058657
PCT Pub. Date: May 7, 2009

(65) Prior Publication Data
US 2010/0225927 A1    Sep. 9, 2010

Related U.S. Application Data

(60) Provisional application No. 60/984,467, filed on Nov. 1, 2007, provisional application No. 60/984,452, filed on Nov. 1, 2007.

(51) Int. Cl.
G01B 11/02 (2006.01)
G01B 9/21 (2006.01)
G01B 11/24 (2006.01)

(52) U.S. Cl.
USPC ............ 356/511; 356/477; 356/496; 356/601

(58) Field of Classification Search
USPC ................ 356/477, 479, 497, 511, 495, 496, 356/601
See application file for complete search history.

(56) References Cited

U.S. PATENT DOCUMENTS 4,168,911 A * 9/1979 Pryor ............................ 356/505
4,964,770 A  10/1990 Steinbichler
(Continued)

FOREIGN PATENT DOCUMENTS

WO  WO 2006/107929 A1 * 10/2006

OTHER PUBLICATIONS

Christensen, et al., "Laser diode coherence length variation for balancing fiber optic interferometers", Jun. 1994, pp. 2034-2038, vol. 33 No. 6, Optical Engineering.

(Continued)

*Primary Examiner* — Gregory J Toatley
*Assistant Examiner* — Dominic J Bologna
(74) *Attorney, Agent, or Firm* — Guerin & Rodriguez, LLP; William G. Guerin

(57) ABSTRACT

Described are an imaging device and method for determining three-dimensional position information of a surface of an object. The device includes a pair of optical fibers, a phase shifter, a detector array and a processor. The phase shifter is coupled to one of the optical fibers and is used to change a phase of optical radiation emitted from the optical fiber relative to a phase of optical radiation emitted from the other optical fiber. The detector array receives optical radiation scattered by the surface of the object. The processor communicates with the detector array and the phase shifter. Signals generated by the detector array are received by the processor and three-dimensional position information for the surface is calculated in response to the received optical radiation scattered by the surface of the object and the change in the relative phase of optical radiation emitted by the optical fibers.

16 Claims, 7 Drawing Sheets

U.S. PATENT DOCUMENTS

| | | | |
|---|---|---|---|
| 5,811,826 A | 9/1998 | Shirley | |
| 5,870,191 A | 2/1999 | Shirley et al. | |
| 5,900,936 A | 5/1999 | Shirley et al. | |
| 6,031,612 A | 2/2000 | Shirley | |
| 6,188,482 B1* | 2/2001 | Cloud | 356/491 |
| 6,690,474 B1 | 2/2004 | Shirley | |
| 6,952,270 B2 | 10/2005 | Shirley | |
| 7,184,149 B2 | 2/2007 | Swanson | |
| 7,242,484 B2 | 7/2007 | Shirley | |
| 7,283,251 B1* | 10/2007 | Tansey | 356/512 |
| 2002/0198457 A1* | 12/2002 | Tearney et al. | 600/476 |
| 2003/0072011 A1* | 4/2003 | Shirley | 356/601 |
| 2006/0012802 A1* | 1/2006 | Shirley | 356/603 |

OTHER PUBLICATIONS

Kotov, et al., "Polarization Modulation of Light in an Optical Waveguide under Lateral Compression", Feb. 21, 2006, pp. 1494-1499, vol. 51, No. 11, Technical Physics, St. Petersburg, Russia.

PCT/US08/80943 International Search Report dated Jan. 5, 2009; 2 pages.

PCT/US08/80943 Written Opinion dated Jan. 5, 2009; 4 pages.

* cited by examiner

OPTICAL FIBER-BASED THREE-DIMENSIONAL IMAGING SYSTEM

RELATED APPLICATIONS

This application claims the benefit of the earlier filing date of U.S. Provisional Patent Application Ser. No. 60/984,452, filed Nov. 1, 2007, titled "High Accuracy Three-Dimensional Imaging of Polished and Translucent Material," and U.S. Provisional Patent Application Ser. No. 60/984,467, filed Nov. 1, 2007, titled "Fiber-Based Accordion Fringe Interferometry," the entireties of which are incorporated herein by reference.

FIELD OF THE INVENTION

The invention relates generally to the measurement of surface contours and more particularly to a non-contact apparatus using optical fiber-based accordion fringe interferometry (AFI) for the three-dimensional measurement of objects.

BACKGROUND OF THE INVENTION

The process for determining the shape of teeth according to traditional dentistry generally includes the use of impression materials, molds or castings. This process is typically slow and prone to material handling errors. After obtaining the impression of the patient's teeth, the mold or impression material is removed from the mouth of the patient and a solid model of the patient's teeth is made from the impression. The impression material or the solid model is sent to a dental laboratory. The solid model is used in the fabrication of one or more corrective or replacement dental components such as artificial teeth, crowns or orthodontic appliances. Inaccuracies and errors introduced at any time during the process can result in an improper fit of the dental component and may limit the ability to secure and retain the dental component in the correct location.

U.S. Pat. No. 4,964,770 describes a process for making artificial teeth. The process includes projecting contour lines onto the patient's teeth and detecting the contour lines using a camera. The location of the projected contour lines is shifted multiple times by a precision motion of the projector and detected by the camera at each position. Camera data are processed to determine contour data for the teeth. The contour data may be provided to a numerically controlled fabrication machine for the generation of the artificial teeth or for orthodontic appliances or for use with dental implantology. The process is subject to inaccuracies as displacement of the contour lines is based on changing the location of the projector. Moreover, the length of time required to obtain the camera data for all sets of contour lines is a significant inconvenience to the dental patient and makes the measurement more sensitive to motion of the projection source, teeth and camera.

Material characteristics of teeth can further limit the ability to obtain accurate three-dimensional data. Teeth are typically translucent therefore a portion of the light incident on the surface of a tooth is scattered from the surface while some of the light penetrates the surface and is internally scattered over a depth below the surface. Furthermore, backscatter can occur at the interface of tooth enamel and dentin if there is sufficient penetration of the incident light. Translucency can prevent an accurate determination of the surface contour of teeth using optical techniques. For example, projected contour lines may appear shifted from their actual location and may have poor contrast. In some instances, translucency causes measurements based on optical techniques to indicate an apparent surface that is beneath the true surface. To overcome difficulties due to translucency, dentists often apply powders such as titanium dioxide to teeth. The application of powder is a further inconvenience that adds more time to the measurement process, introduces measurement uncertainty and can interfere with adhesives or other bonding agents used to fasten the replacement tooth.

SUMMARY OF THE INVENTION

In one aspect, the invention features a method for determining three-dimensional position information of a surface of an object. The surface of the object is illuminated with radiation emitted from a pair of optical fibers. The radiation emitted from each optical fiber is coherent with respect to the radiation emitted from the other optical fiber. Radiation scattered from the surface of the object is detected. A phase of the radiation emitted from one of the optical fibers relative to a phase of the radiation emitted from the other optical fiber as determined at a point on the surface of the object is changed before again detecting radiation scattered by the surface of the object. Three-dimensional position information of the surface of the object is calculated in response to the change of the phase and the radiation detected before and after the change of the phase.

In another aspect, the invention features an imaging device for determining three-dimensional position information of a surface of an object. The device includes first and second optical fibers, a phase shifter, a detector array and a processor. Each optical fiber has an exit end and is adapted to receive optical radiation. The optical radiation received by the first and second optical fibers is mutually coherent. The phase shifter is coupled to the first optical fiber to change a phase of optical radiation emitted from the exit end of the first optical fiber relative to a phase of optical radiation emitted from the exit end of the second optical fiber. The detector array receives optical radiation scattered by the surface of the object. The processor communicates with the detector array and the phase shifter, and receives signals generated by the detector array. The processor calculates three-dimensional position information in response to the received optical radiation scattered by the surface of the object and a change in the phase of optical radiation emitted from the exit end of the first optical fiber relative to a phase of optical radiation emitted from the exit end of the second optical fiber.

BRIEF DESCRIPTION OF THE DRAWINGS

The above and further advantages of this invention may be better understood by referring to the following description in conjunction with the accompanying drawings, in which like numerals indicate like structural elements and features in the various figures. The drawings are not necessarily to scale, emphasis instead being placed upon illustrating the principles of the invention.

DETAILED DESCRIPTION

In brief overview, the present invention relates to a device based on accordion fringe interferometry (AFI) principles that are useful for real-time three-dimensional imaging of objects. The device can be used in a wide variety of applications including, for example, intra-oral imaging for restorative dentistry and orthodontics, handheld three-dimensional scanners and probes for industrial applications such as measurement and inspection, and compact three-dimensional machine vision sensors. Compact and substantially insensitive to motion between the device and the objects to be measured, the device is advantageously adapted for scanning translucent objects and intra-oral surfaces such as the surfaces of teeth, gum tissue and various dental structures and materials.

The device can be fabricated from inexpensive components used in the high volume consumer electronics and telecommunications industries. In one embodiment, portions of the device are packaged as a small wand that is easily held and maneuvered by a dental professional. A remote electrical power supply and optical source enable a more compact wand. Although the device utilizes AFI measurement techniques as described in U.S. Pat. No. 5,870,191 to Shirley et al., the device does not use a grating and lens to generate coherent point sources of radiation as in other AFI configurations. Instead, radiation is emitted from a pair of optical fibers and is used to illuminate objects to be measured with interferometric fringes. Consequently, movement of a macroscopic grating which requires several milliseconds or more to effect a phase shift is unnecessary. A fiber-based phase shifter is used to change the relative phase (i.e., the difference in phase) of the radiation emitted from the exit ends of the two optical fibers in a few microseconds or less. Optical radiation scattered from surfaces and subsurface regions of illuminated objects is received by a detector array. Electrical signals are generated by the detector array in response to the received radiation. A processor receives the electrical signals and calculates three-dimensional position information of object surfaces based on changes in the relative phase of the emitted optical radiation and the received optical radiation scattered by the surfaces. The device preferably utilizes a source of optical radiation having a wavelength between about 350 nm and 500 nm to reduce measurement error associated with penetration of the incident radiation into the subsurface regions of translucent objects.

Figure 1:
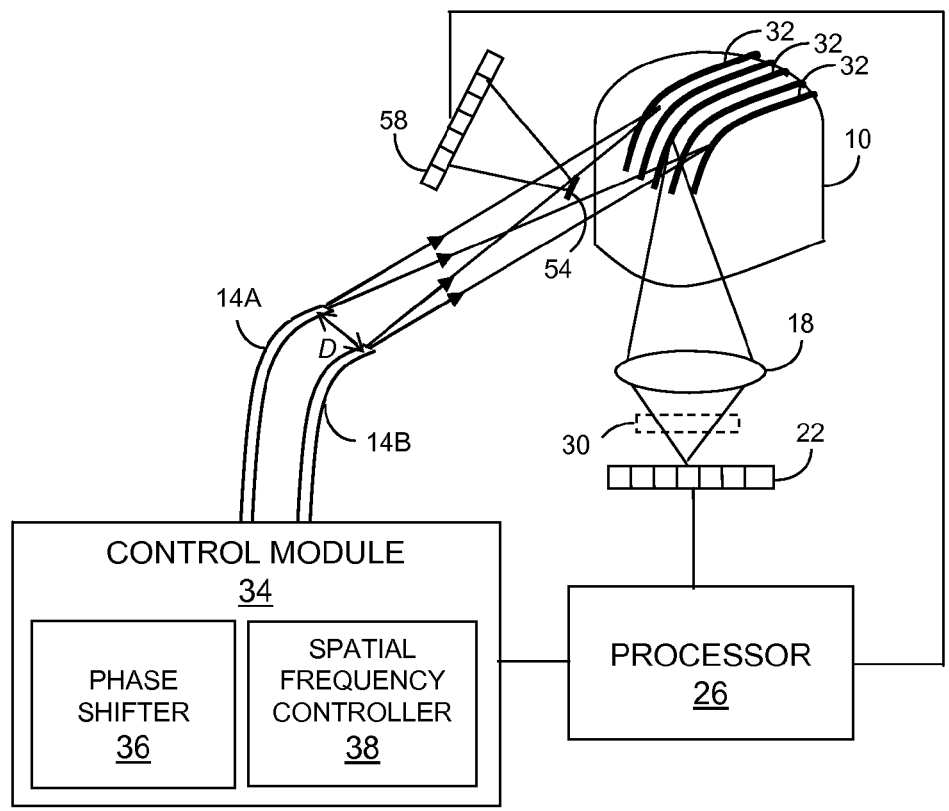
FIG. 1 illustrates an embodiment of an imaging device for determining three-dimensional position information of a surface of an object according to the invention
Figure 2:
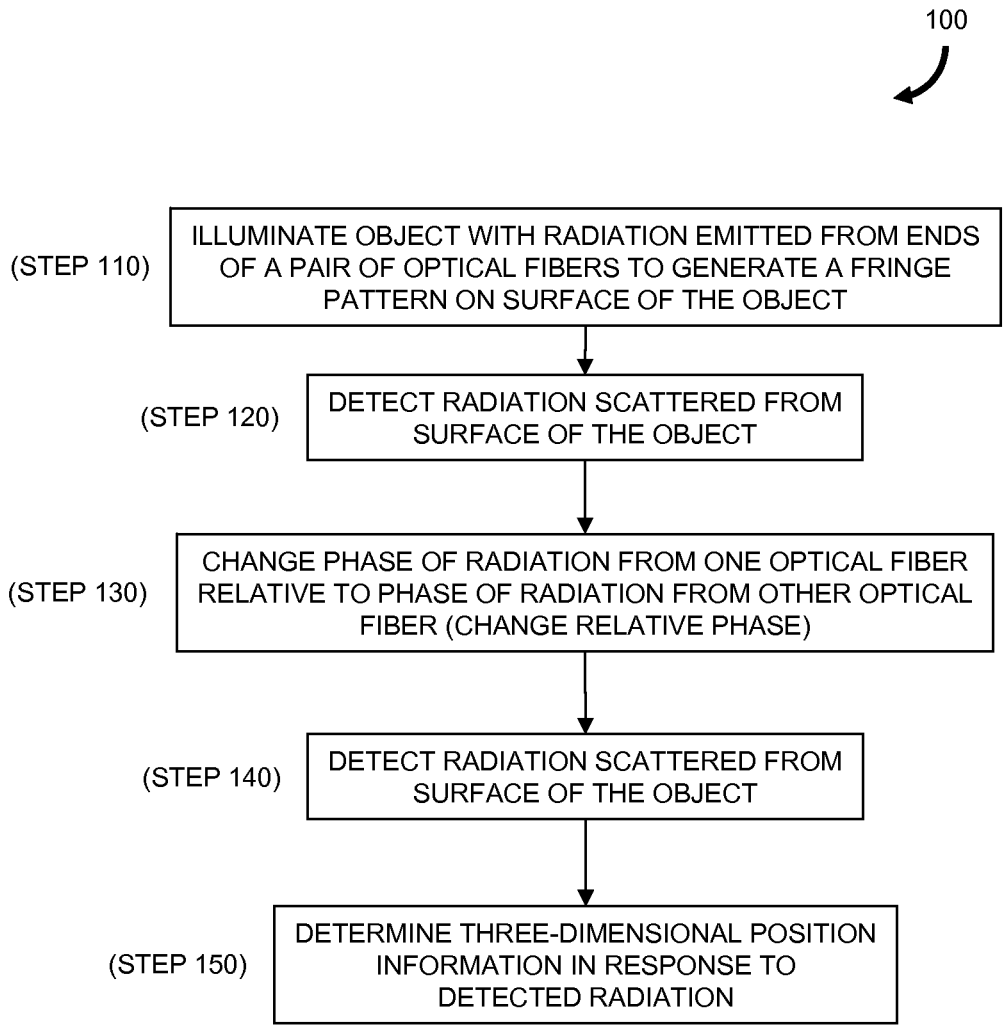
FIG. 2 is a flowchart representation of an embodiment of a method for determining three-dimensional position information of a surface of an object according to the invention.

FIG. 1 illustrates an embodiment of an imaging device for determining three-dimensional position information of a surface of an object 10 according to the invention. FIG. 2 is a flowchart representation of an embodiment of a method 100 for determining three-dimensional position information of a surface of an object (e.g., object 10) according to the invention. In the illustrated embodiment, the object 10 is a translucent object such as an intra-oral object (i.e., an object located in the mouth of a patent). For example, the object 10 may be a natural or artificial tooth. Optical radiation is launched into a pair of single mode optical fibers 14A and 14B from a master optical source (not shown). In one embodiment, the optical fibers 14 are coupled by a fiber splitter so that optical radiation is launched into an input end of a single optical fiber. The object 10 is illuminated (step 110) with the diverging radiation emitted from the exit ends of the fibers 14. In one embodiment, the radiation emitted from the two fibers 14 is polarized in a common orientation.

Some of the radiation incident on the translucent object 140 is scattered from the surface while some of the radiation penetrates into a subsurface region (i.e., a volume below the surface) where it is scattered. An image of the surface of the object 10 is formed by an imaging element or lens 18 on an array of photodetectors 22 such as a two-dimensional charge coupled device (CCD) imaging array. The detector array 22 provides an output signal to a processor 26. The output signal includes information on the intensity of the radiation received (steps 120 and 140) at each photodetector in the array 22. An optional polarizer 30 is oriented to coincide with the main polarization component of the scattered radiation. A control module 34 controls the operation of the radiation emitted from the optical fibers 14. The control module 34 includes a phase shifter 36 that adjusts (step 130) the relative phase of the radiation emitted by the two fibers 14 as determined at the surface of the object 10. The control module 34 also includes a spatial frequency controller 38 that adjust the pitch of interference fringes 32 in the illumination pattern at the object surface. The fringes 32 are the result of interference of the coherent radiation emitted from the optical fibers 14. The spatial frequency of the fringe pattern, i.e., the inverse of the separation of the fringes 32, is determined by the separation D of the ends of the optical fibers 14, the distance from the ends of the fibers to the object, and the wavelength of the radiation. The processor 26 and control module 34 communicate to coordinate the processing of signals from the photodetector array 22 with respect to changes to the spatial frequency and the relative phase, and the processor 26 determines (step 150) the three-dimensional information for the surface according to the detected radiation. In a preferred embodiment, the processor 26 includes multiple central processing units ("CPUs") for parallel processing to increase the data processing rate and to output the final measurement data in less time.

Figure 3:
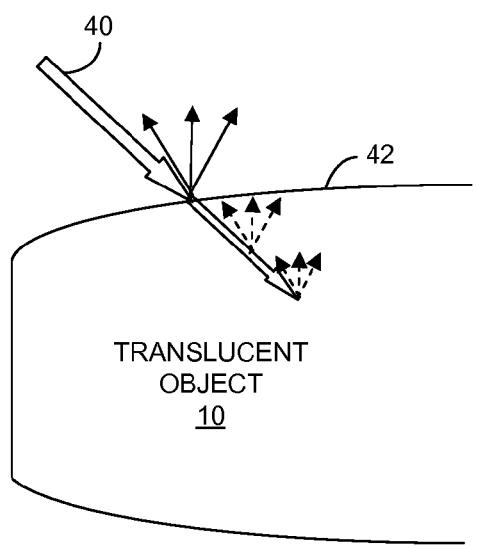
FIG. 3 is a vector illustration of radiation from the two single mode optical fibers of FIG. 1 as incident on the surface of a translucent object.

FIG. 3 is a vector illustration of the radiation 40 from the two single mode optical fibers as incident on the surface 42 of the translucent object 10. A portion of the incident radiation 40 is scattered from the surface 42 while a portion of the incident radiation 40 penetrates and is scattered from within the object 10 below the surface 42. The wavelength of the incident radiation, and the wavelength-dependent reflectance characteristic and wavelength-dependent transmittance characteristic of the object material, determine the relative contributions to the radiation scattered from the object surface 42 and the radiation scattered within the subsurface region.

Referring also to FIG. 1, the photodetector array 22 receives an image of the fringe pattern projected onto the surface 42 of the object 10; however, the radiation scattered in the subsurface region degrades the image of the fringe pattern. If the scattered radiation contribution from the subsurface region is significant relative to the scattered radiation contribution from the surface 42, the apparent location (i.e., apparent phase) of the fringe pattern on the surface 42 can be different than the actual location. The method of the invention exploits a counter-intuitive approach to reducing measurement errors due to translucent internal scatter by utilizing an illumination wavelength which increases internal scatter near the surface. The illumination wavelength exhibiting a high coefficient of internal scattering is combined with a high spatial frequency fringe pattern such that a nearly uniform photon flux is created just below the surface. The subsurface scatter contributes a substantially constant background to the image of the surface 42 at the photodetector array 22. The background contribution is ignored by the phase analysis, and the magnitude of the residual error induced by any remaining spatially-varying intensity contribution is further reduced in significance if the contribution is close to the surface 42. Measurements performed according to the method of the invention provide greater accuracy when using radiation having a wavelength predetermined from the wavelength-dependent reflectance characteristic and wavelength-dependent transmittance characteristic of the object material to improve the surface scattering contribution relative to the subsurface scattering contribution.

For three-dimensional imaging of living, natural teeth, wavelengths in the lower visible and near ultraviolet (UV) range (e.g., 350 to 500 nm) provide a higher coefficient of subsurface scattering than longer wavelengths due to the wavelength-dependent characteristics of enamel and dentin. In one embodiment of an intra-oral imaging device, the radiation source is a commercially-available blue laser diode having an operating wavelength of 405 nm (e.g., model no. BCL-050-405 available from Crystal Laser of Reno, Nev.).

In another embodiment of an intra-oral imaging device, the spatial frequency of the fringe pattern at the surface 42 is predetermined so that subsurface scattering of radiation that penetrates the object 10 from one fringe overlaps the subsurface scatter from the two neighboring fringes, and thus diffuses the fringes 32 that propagate below the surface. As a result, the scattered subsurface radiation provides a substantially constant background to the detected fringe pattern. In a preferred embodiment, the spatial frequency of the fringe pattern is at least 1 fringe/mm.

Figure 4A:
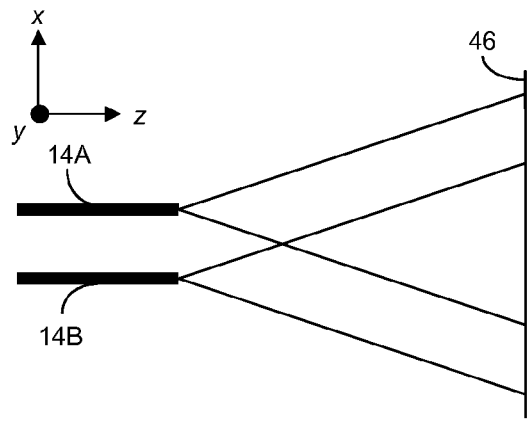
FIG. 4A illustrates the illumination of a flat surface by a pair of optical fibers.
Figure 4B:
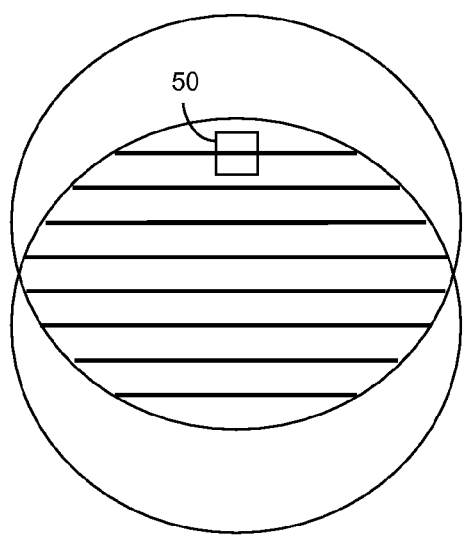
FIG. 4B illustrates the fringe pattern at the flat surface of FIG. 4A.
Figure 4C:
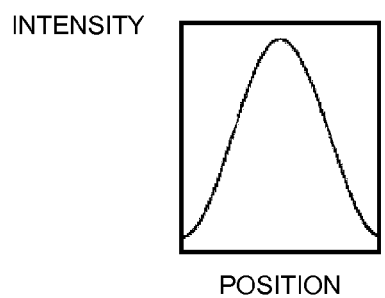
FIG. 4C illustrates the vertical intensity profile of a portion of the fringe pattern depicted in FIG. 4B.
Figure 5A:
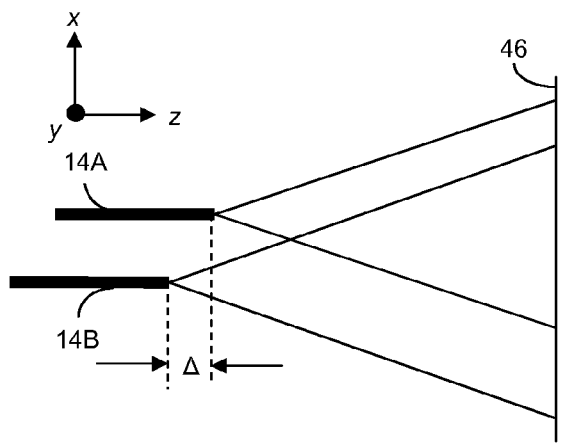
FIG. 5A shows the displacement of an optical fiber to change the relative phase of the radiation emitted from the two optical fibers of FIG. 4A.
Figure 5B:
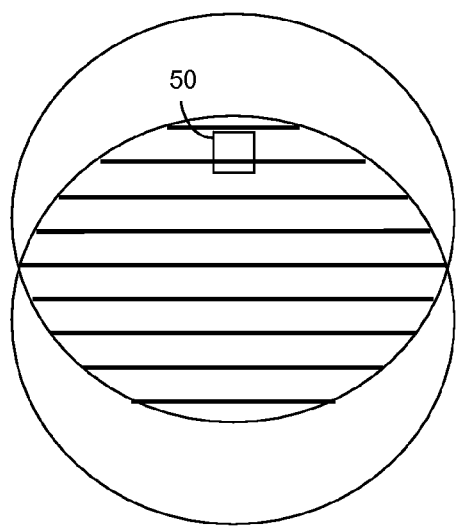
FIG. 5B illustrates a lateral shift of the fringe pattern of FIG. 4B due to a change in the relative phase of the radiation emitted from the two optical fibers according to FIG. 5A.
Figure 5C:
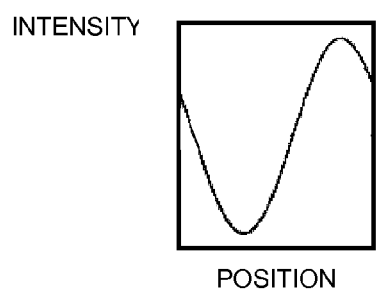
FIG. 5C illustrates the vertical intensity profile for a portion of the fringe pattern depicted in FIG. 5B.

FIG. 4A illustrates how radiation emitted from a pair of single mode optical fibers 14 illuminates a flat surface 46 resulting in the fringe pattern shown in FIG. 4B where a dark horizontal line indicates the greatest intensity for each fringe. The fringes have a sinusoidal intensity profile as shown in FIG. 4C for a vertical slice through the boxed region 50 of FIG. 4B. To rapidly change the relative phase of the radiation emitted from the two fibers 14, the phase shifter 36 includes a translation module to move the end of one of the fibers 14B along the fiber axis (i.e., z-axis) to displace the end of the fiber 14B from its original position by a distance Δ as shown in FIG. 5A. Thus if the fiber end is moved through a distance that is one-third of the wavelength λ (i.e., Δ=λ/3) of the radiation, the relative phase shift is 120°. FIGS. 5B and 5C illustrate the shift in the fringe pattern that results from a 120° phase shift. In one embodiment, the mechanism used to translate the fiber end is a translation stage that can accurately position the end of the fiber 14B along the z-axis in either direction.

Figure 5D:
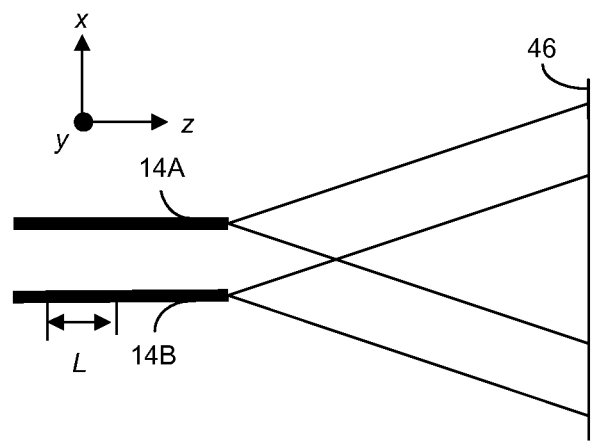
FIG. 5D illustrates a fiber stretching technique for changing the relative phase of the radiation emitted from the two optical fibers of FIG. 4A.

FIG. 5D illustrates a different technique for obtaining a relative phase shift. In this technique, the phase shifter 36 includes a fiber stretch mechanism to stretch one of the optical fibers 14B along a length L while its end remains fixed in location. The stretching alters the physical properties of the fiber 14B such as its length, index of refraction, and birefringence. As a result, the effective optical path length of the fiber 14B is changed and the phase of the radiation emitted from the fiber 14B is changed relative to the phase of the radiation emitted from the other fiber 14A. This change in the relative phase results in a lateral shift of the fringe pattern as shown, for example, in FIG. 5B and FIG. 5C. In an alternative embodiment, the phase shifter 36 includes a fiber compression mechanism to compress or "pinch" one of the optical fibers 14 along a radial fiber axis (i.e., an axis in the x-y plane).

Figure 6A:
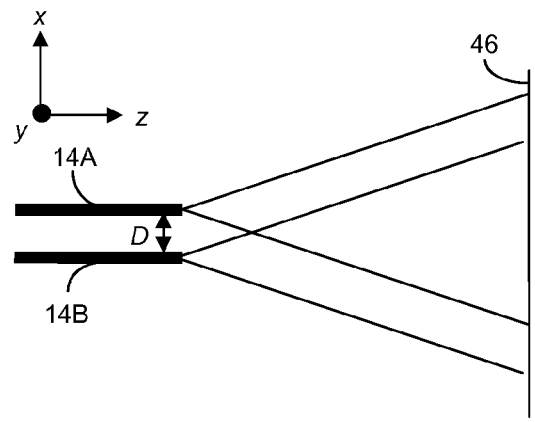
FIG. 6A shows a change in the separation of the fiber ends of the two optical fibers of FIG. 4A used to modify the spatial frequency of a fringe pattern.
Figure 6B:
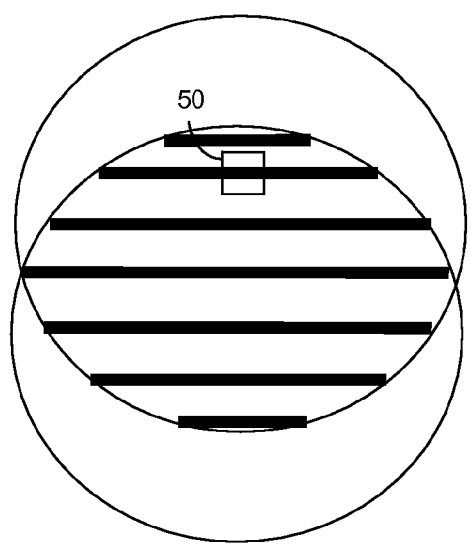
FIG. 6B illustrates the fringe pattern resulting from the configuration of optical fibers shown in FIG. 6A.
Figure 6C:
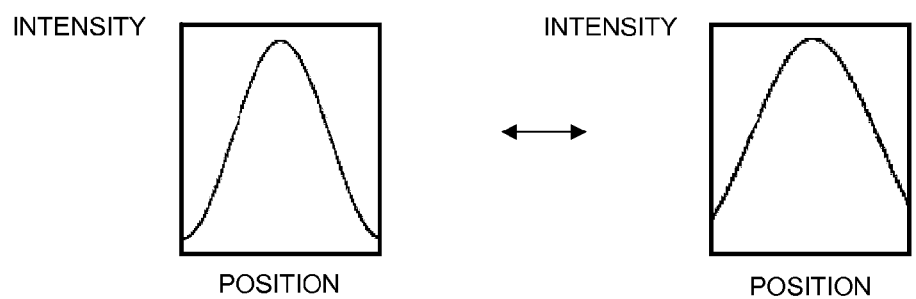
FIG. 6C illustrates vertical intensity profiles for a portion of the fringe patterns depicted in FIG. 4B and FIG. 6B.

For a constant wavelength, the spatial frequency of the fringe pattern is adjusted by controlling the separation D of the fiber ends. FIG. 6A shows how the separation D of the fiber ends is decreased relative to the fibers 14 of FIG. 4A. As a result, the fringe pattern and the fringes within the fringe pattern are broadened as shown in FIG. 6B and FIG. 6C. In one embodiment, the spatial frequency controller 38 (FIG. 1) includes a translation module to translate the end of at least one of the optical fibers 14 along a transverse axis defined between the fiber ends (i.e., the illustrated x-axis) in either direction. The separation distance D is decreased to reduce the spatial frequency or increased to increase the spatial frequency. Preferably, both fiber ends are translated equal distances in opposite directions so that the position of the midpoint between the fiber ends is unchanged and the fringe pattern is not laterally shifted.

Figure 7:
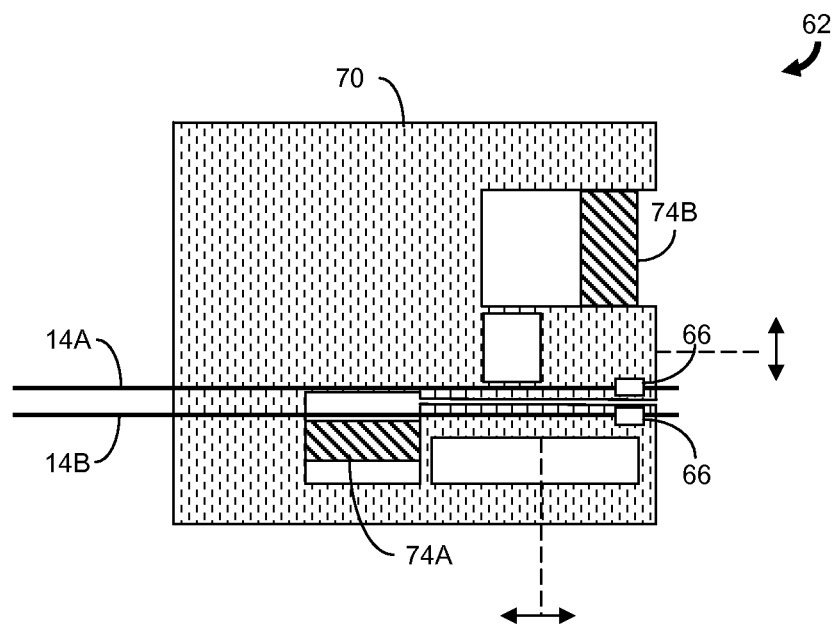
FIG. 7 illustrates a structure for use in an embodiment of an intra-oral device according to the invention.

FIG. 7 illustrates a structure 62 having axial and lateral flexures for use in an embodiment of an intra-oral device according to the invention. Two single mode optical fibers 14 are fixed by clamps 66 to a substrate 70. The substrate 70 can be fabricated from aluminum or another material depending on the tolerance to temperature variations and fabrication capabilities. Two piezoelectric actuators 74A and 74B are secured to the substrate 70. The actuators 74 provide a means to change the separation distance between the exit ends of the optical fibers 14 and to change the axial position of the exit end of one fiber 14B. Initially, a control signal is applied to each actuator 74 to adjust its position approximately to a midrange position within an operating range (e.g., ±1 μm range). Optical fiber 14A is then clamped to the lateral flexure portion of the substrate 70. Next, optical fiber 14B is positioned and adjusted along its fiber axis to maximize the contrast of the fringe pattern, and then clamped to the axial flexure portion of the substrate 70. During measurements, the axial piezoelectric actuator 74A adjusts the axial position of the end of the optical fiber 14B over a portion of the actuator range to cause a shift in the relative phase by the desired amount (e.g., +120° and −120°). The lateral piezoelectric actuator 74B adjusts the separation of the ends of the two fibers 14 within a range of ±1 μm to cause a change in the spatial frequency of the fringe pattern by a desired value.

Figure 8:
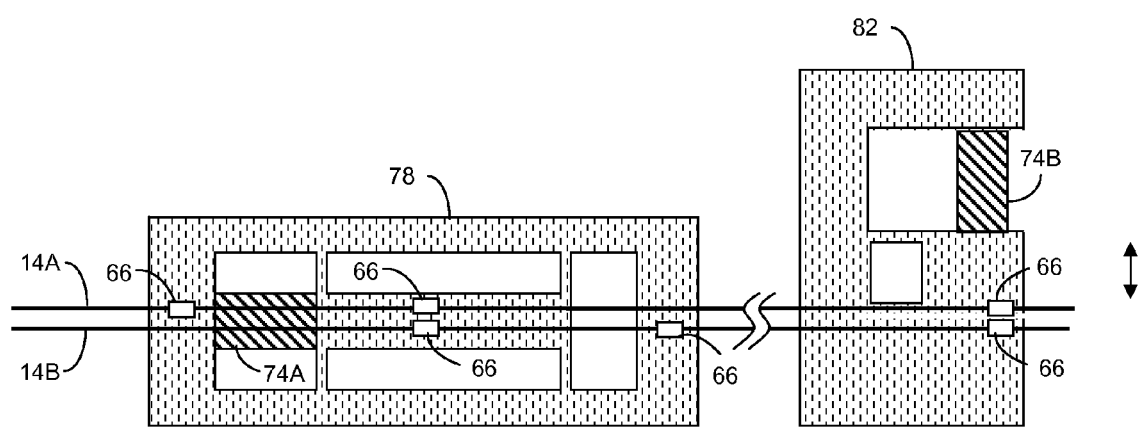
FIG. 8 illustrates a configuration of two structures for use in an embodiment of an intra-oral device according to the invention.

FIG. 8 illustrates a device configuration employing two structures 78 and 82 for use in an embodiment of an intra-oral device according to the invention. The two single mode optical fibers 14 are fixed by clamps 66 to structures 78 and 82. One piezoelectric actuator 74B is integrated into one structure 82 to enable a controlled change in the separation distance between the ends of the optical fibers 14. The other piezoelectric actuator 74A is used to stretch an optical fiber 14A (as described for FIG. 4D) and thereby change the relative phase between the radiation emitted from the ends of the two fibers 14. During initial configuration setup, control signals position the actuators 74 near the midpoints of their respective ranges of motion. Optical fiber 14B is then clamped to the structure 78 near the center of the lateral flexure portion and near the exit end. Optical fiber 14A is then clamped to the structure 78 near the center of the lateral flexure and near the entrance end. The axial piezoelectric actuator 74A is used to stretch one optical fiber 14A on expansion and to stretch the other optical fiber 14B on contraction. Stretching of the optical fibers 14 in this manner causes a shift in the relative phase of the radiation emitted from the ends of the fibers 14 by the desired amount (e.g., +120° and −120°). As the fiber clamps 66 are in contact with the sheathing of each fiber 14, the linear motion of the actuator 74A generally is substantially greater than the actual increase in length of the stretched optical fiber 14. Furthermore, the optical path length of the optical radiation is dependent on the length and the index of refraction of each optical fiber 14. Consequently, the desired relative phase shift is preferably determined by calibrating an initial position for each phase, and then by dynamically tracking fringe motion and applying a compensation offset.

In an alternative embodiment, a second separation of the optical fibers 14 is effectively accomplished by selectively enabling a third optical fiber (not shown) spaced the proper distance from the first fiber 14B. Thus the translation mechanism can be eliminated.

After completing attachment to the first structure 78, the optical fibers 14 are attached to the second structure 82 that includes a lateral piezoelectric actuator 74B for achieving a desired separation of the fiber ends. In one embodiment, the first and second structures 78 and 82 are separated by at least 50 mm to provide sufficient slack in the two optical fibers 14 so that motion of one actuator 74 does not affect the control of the fibers 14 by the other actuator 74.

Environmental instability can limit the ability to perform accurate measurements using AFI principles. In particular, measurement accuracy is degraded according to the error between the commanded phase shift and the actual phase shift applied to the fringe pattern. The phase shifting techniques described above impart a small optical path length difference of a few hundred nanometers or less between the two radiation beams. Consequently, temperature drift and mechanical creep can be sources of error in the relative phase. Capacitance gauges can be used to monitor axial shifts in optical fiber position and stretching or compression actuation for the phase shifting techniques described above; however, in some embodiments such electro-mechanical monitoring may not accurately correspond to changes imparted to the relative phase.

In a preferred embodiment, a control system based on fringe monitoring is used to establish the desired relative phase and to maintain fringe stability. Referring again to FIG. 1, a portion of the fringe pattern is "sampled" by an optical element 54 and received by a fringe position sensor 58 that determines the location of a fringe within a small region of the fringe pattern. In one embodiment, the fringe position sensor 58 is a detector array. In other embodiments the fringe position sensor includes a configuration of one or more detectors that can sense a change in the position of a fringe. In another embodiment, the fringe pattern detector may be a section of the detector array 22. The fringe position detector array 58 can have a low pixel count as only one fringe in the fringe pattern is monitored. The optical element 54 can be a mirror having a dimension that is approximately equal to the width of a fringe at the mirror. The reflected radiation is directed to the detector array 58 which provides image data to the processor 26. The image data are processed to monitor the location of the sampled fringe in the field of view of the detector array 58. If the processor 26 determines that the fringe is "drifting" and therefore that there is a displacement error in the fringe pattern, the phase shifter 36 adjusts the relative phase to counteract the drift. Thus the displacement error is substantially cancelled and the fringe pattern remains stable.

While the invention has been shown and described with reference to specific embodiments, it should be understood by those skilled in the art that various changes in form and detail may be made therein without departing from the spirit and scope of the invention.

What is claimed is:

1. A method for determining three-dimensional position information of a surface of an object, the method comprising:
   projecting a fringe pattern from a pair of optical fibers to illuminate a surface of an object, the fringe pattern being generated by the interference of optical radiation emitted from each of the optical fibers;
   monitoring the location of at least one fringe in the fringe pattern to determine a displacement error of the fringe pattern;
   changing a phase of the optical radiation emitted from one of the optical fibers relative to a phase of the optical radiation emitted from the other optical fiber to reduce the displacement error and stabilize the fringe pattern;
   detecting optical radiation scattered from the illumination of the surface of the object with the fringe pattern;
   changing the phase of the optical radiation emitted from one of the optical fibers relative to the phase of the radiation emitted from the other optical fiber to cause a predetermined phase shift in the fringe pattern;
   detecting optical radiation scattered by the surface of the object after the predetermined phase shift in the fringe pattern; and
   calculating three-dimensional position information of the surface of the object in response to the change of the phase to cause the predetermined phase shift in the fringe pattern and in response to the optical radiation detected before and after the predetermined phase shift in the fringe pattern.

2. The method of claim 1 wherein changing the phase of the optical radiation emitted from one of the optical fibers relative to the phase of the optical radiation emitted from the other optical fiber comprises translating an end of one of the optical fibers along a fiber axis.

3. The method of claim 1 wherein changing the phase of the optical radiation emitted from one of the optical fibers relative to the phase of the optical radiation emitted from the other of the optical fibers comprises stretching one of the optical fibers along a fiber axis.

4. The method of claim 1 wherein changing the phase of the optical radiation emitted from one of the optical fibers relative to the phase of the optical radiation emitted from the other of the optical fibers comprises compressing one of the optical fibers along a radial fiber axis.

5. The method of claim 1 further comprising changing a spatial frequency of the fringe pattern.

6. The method of claim 5 wherein each optical fiber has an end separated from an end of the other optical fiber along a transverse axis and wherein changing the spatial frequency of the fringe pattern comprises translating the end of at least one of the optical fibers along the transverse axis.

7. An imaging device for determining three-dimensional position information of a surface of an object, the imaging device comprising:

a pair of optical fibers comprising a first optical fiber and a second optical fiber each configured to emit optical radiation, the pair of optical fibers configured to project a fringe pattern for illuminating a surface of an object;

a phase shifter coupled to the first optical fiber to change a phase of the optical radiation emitted from the first optical fiber relative to a phase of the optical radiation emitted from the second optical fiber;

a detector array to receive optical radiation scattered by the surface of the object illuminated with the fringe pattern;

a fringe position sensor; and a processor in communication with the detector array, the phase shifter and the fringe position sensor, the processor receiving a signal from the fringe position sensor indicating a phase error in the fringe pattern and adjusting the phase of the optical radiation emitted from the first optical fiber in response thereto, the processor receiving signals generated by the detector array and calculating three-dimensional position information in response to the received optical radiation scattered by the surface of the object and the change in the phase of the optical radiation emitted from the first optical fiber relative to the phase of the optical radiation emitted from the second optical fiber.

8. The imaging device of claim 7 wherein the phase shifter comprises a translation module coupled to the first optical fiber and adapted for changing a position of an exit end of the first optical fiber along a fiber axis.

9. The imaging device of claim 7 wherein the phase shifter comprises a fiber stretch mechanism coupled to the first optical fiber and adapted for stretching a length of the first optical fiber.

10. The imaging device of claim 7 wherein the phase shifter comprises a fiber compression mechanism coupled to the first optical fiber and adapted for compressing the first optical fiber along a radial fiber axis.

11. The imaging device of claim 7 wherein each of the first and second optical fibers has an exit end, the imaging device further comprising a translation module coupled to one of the first and second optical fibers to change a separation of the exit ends and thereby to change a spatial frequency of the fringe pattern.

12. The imaging device of claim 7 further comprising a source of optical radiation in communication with the first and second optical fibers.

13. The imaging device of claim 7 wherein the fringe position sensor comprises a second detector array.

14. The imaging device of claim 7 wherein the fringe position sensor comprises a section of the detector array.

15. The imaging device of claim 7 further comprising an optical element disposed between the pair of optical fibers and the object to direct a portion of the fringe pattern to the fringe position sensor.

16. The imaging device of claim 15 wherein the optical element is a mirror.

* * * * *